United States Patent
Liu et al.

(10) Patent No.: US 10,059,649 B2
(45) Date of Patent: Aug. 28, 2018

(54) METHOD FOR PRODUCING ETHANOL AND COPRODUCING METHANOL

(71) Applicant: DALIAN INSTITUTE OF CHEMICAL PHYSICS, CHINESE ACADEMY OF SCIENCES, Dalian (CN)

(72) Inventors: Yong Liu, Dalian (CN); Wenliang Zhu, Dalian (CN); Hongchao Liu, Dalian (CN); Youming Ni, Dalian (CN); Zhongmin Liu, Dalian (CN); Shuanghe Meng, Dalian (CN); Lina Li, Dalian (CN); Shiping Liu, Dalian (CN); Hui Zhou, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 253 days.

(21) Appl. No.: 15/103,076

(22) PCT Filed: Dec. 16, 2013

(86) PCT No.: PCT/CN2013/089539
§ 371 (c)(1),
(2) Date: Jun. 9, 2016

(87) PCT Pub. No.: WO2015/089704
PCT Pub. Date: Jun. 25, 2015

(65) Prior Publication Data
US 2016/0311740 A1    Oct. 27, 2016

(51) Int. Cl.
| | | |
|---|---|---|
| *C07C 29/154* | (2006.01) |
| *C07C 29/149* | (2006.01) |
| *B01J 23/72* | (2006.01) |
| *B01J 23/78* | (2006.01) |
| *B01J 23/80* | (2006.01) |
| *B01J 23/86* | (2006.01) |
| *B01J 23/889* | (2006.01) |
| *C07C 29/156* | (2006.01) |

(52) U.S. Cl.
CPC ............. *C07C 29/154* (2013.01); *B01J 23/72* (2013.01); *B01J 23/78* (2013.01); *B01J 23/80* (2013.01); *B01J 23/868* (2013.01); *B01J 23/8892* (2013.01); *C07C 29/149* (2013.01); *C07C 29/156* (2013.01); *C07C 2521/04* (2013.01); *C07C 2521/10* (2013.01); *C07C 2523/02* (2013.01); *C07C 2523/06* (2013.01); *C07C 2523/26* (2013.01); *C07C 2523/28* (2013.01); *C07C 2523/34* (2013.01); *C07C 2523/72* (2013.01); *C07C 2523/745* (2013.01); *C07C 2523/755* (2013.01); *Y02P 20/52* (2015.11)

(58) Field of Classification Search
CPC ... C07C 29/154; C07C 29/149; C07C 29/156; B01J 23/72; B01J 23/78; B01J 23/80; B01J 23/868; B01J 23/8892
USPC ........................................................ 568/876
See application file for complete search history.

(56) References Cited

FOREIGN PATENT DOCUMENTS

| CN | 101020139 A | | 8/2007 |
|---|---|---|---|
| CN | 101185895 A | | 5/2008 |
| CN | 1011858895 A | * | 5/2008 |
| CN | 102872878 A | * | 1/2013 |
| CN | 102872878 A | | 1/2013 |
| CN | 103288594 A | | 9/2013 |
| JP | 2008239539 A | | 10/2008 |

OTHER PUBLICATIONS

M. Ojeda et al., Applied Catalysis A: General 261 (2004), 47-55.
M.A. Haider et al., Journal of Catalysis 261 (2009), 9-16.
X. Pan et al., Nature Materials 6 (2007), 507-511.
W. Chen et al., Applied Catalysis A: General 407 (2011), 231-237.
H. Yin et al., Applied Catalysis A: General 243 (2003), 155-164.
J. Fox et al., Journal of Catalysis 90 (1984), 127-138.
G. Jenner et al., Journal of Molecular Catalysis A: Chemical 96 (1995), 215-222.
X. Li et al., ChemSusChem 3 (2010), 1192-1199.

* cited by examiner

*Primary Examiner* — Deborah D Carr
(74) *Attorney, Agent, or Firm* — Enshan Hong; VLP Law Group LLP

(57) ABSTRACT

A method for producing ethanol and coproducing methanol on a catalyst in a reactor using a co-feed of a synthesis gas and acetate as a reaction raw material comprising passing a raw material gas containing an acetate and a synthesis gas through a reactor loaded with a catalyst to produce ethanol and coproduce methanol under conditions of a reaction temperature of 150-350° C., a reaction pressure of 0.1-20.0 MPa, a reaction volume hourly space velocity of 100-45000 $mlg^{-1}h^{-1}$, and an acetate weight hourly space velocity of 0.01-5.0 $h^{-1}$; and the active components of the catalyst are copper and optionally zinc and/or aluminum, which greatly facilitates the conversion of carbon monoxide to methanol, while an extremely high activity of acetate hydrogenation is maintained.

8 Claims, No Drawings

METHOD FOR PRODUCING ETHANOL AND COPRODUCING METHANOL

RELATED APPLICATIONS

This is a U.S. national stage of international application No. PCT/CN2013/089539 filed on Dec. 16, 2013.

FIELD OF THE INVENTION

This disclosure pertains to the field of catalytic chemistry, and specifically to a new method for producing ethanol and coproducing methanol.

BACKGROUND OF THE INVENTION

Ethanol is mainly used as a vehicle fuel and a vehicle fuel additive, and at the meanwhile it is an important organic chemical raw material and is mainly used for the production of acetaldehyde, ethyl ether, acetic acid, ethyl acetate, ethylamine, or the like. The global production of ethanol in 2012 is up to 85.1 billion liters, while ethanol-gasoline in China has accounted for 20% or more of the total amount of gasoline consumption in China. During the twelfth five-year plan, the proportion for which the non-fossil energies in China account in the primary energies will increase to 11.4%, and at the meanwhile new fuel ethanol projects with crops as mainly raw materials will be no longer constructed. Therefore, the synthesis of ethanol from a plurality of pathways has important realistic sense and strategic sense for saving petroleum resources and reducing environmental pollution.

At present, the industrial methods for producing ethanol include fermentation method and ethylene hydration method (the ethanol, either prepared by fermentation method or ethylene hydration method, is typically an azeotrope of ethanol and water, and further dehydration is required to obtain absolute ethanol). The main raw materials of fermentation method are plants such as sugar cane, cassava, corn, etc. A large amount of corn in the United States is used to produce ethanol fuel, resulting in short supply and increased price of crops in the world. Therefore, a number of countries limit bioethanol projects to some extent. The ethylene hydration method uses phosphoric acid carried on silica gel or diatomaceous earth as a catalyst, and this process is firstly industrialized by Shell Corporation in 1947. Broadening sources of ethanol raw materials and reducing the dependence on petroleum resources have become hot spots of studies. It is considered to be one of the most promising schemes to directly prepare ethanol from a synthesis gas [Appl. Catal. A 261 (2004) 47, J. Catal. 261 (2009) 9]. Pan et al., [Nat. Mater. 6 (2007) 507] reports a Rh precious metal catalyst selectively carried on the inner wall of a carbon nanotube, which greatly increases the yield of ethanol directly prepared from synthesis gas. However, its further application is limited due to the use of the expensive precious metal Rh. Another scheme is to directly prepare ethanol from synthesis gas. On Nov. 1, 2011, a research and development project of a set of technique for preparing ethanol from at 30 thousand tons per year was started to be constructed by Jiangsu Suopu Group. This technique are developed by Dalian Institute of Chemical and Physics, Chinese Academy of Sciences, which indicates that this technique has been fully in the stage of industrial representative practice. After the project is established, it will be the first set of industrialized apparatus for preparing ethanol from coal through synthesis gas on an order of 10 thousand tons in the world. However, this scheme uses a catalyst of precious metal rhodium and the cost of the catalyst is relatively high. Furthermore, strictly, the product is mixed C1-C5 alcohols, and the selectivity of ethanol is less than 80% [Appl. Catal. A 407 (2011) 231, Appl. Catal. A 243 (2003) 155]. In addition, the homologation reaction for preparing ethanol from methanol is also intensively studied, and this scheme uses Co or Ru as a catalyst and an iodide as a promoter to perform reaction in a homogeneous system [J. Catal. 90 (1984)127, J. Mol. Catal. A 96 (1995) 215]. However, due to severe corrosion of apparatuses by iodides as well as complex reaction products and low selectivity of ethanol, the application of this method is limited to some extent.

In the newest scheme for directly synthesizing ethanol from synthesis gas, dimethyl ether is used as a raw material, methyl acetate is directly synthesized by carbonylation reaction, and ethanol is then prepared by hydrogenation. At present, this scheme is still in the research period, but it has remarkably large prospect for application. Recently, Tsubaki et al., [JP2008239539, ChemSusChem 3 (2010) 1192] achieves direct generation of ethanol from DME on H-MOR and Cu/ZnO catalysts, and it has been studied and found that the two catalysts have synergistic effect.

Methanol is also an important chemical raw material and a vehicle fuel additive, and is mainly used as a solvent and in the preparation of formaldehyde, acetic acid, and dimethyl ether and the process of MTG, MTO, etc. In 2011, the production of methanol in China is up to 20.35 million tons, and it is estimated that the production of methanol will further increase in the future as techniques such as MTO and the like are generalized. At present, the synthesis of methanol is achieved with a copper-based catalyst in a fixed bed reactor at 240-260° C. and 5-10 MPa.

At present, dimethyl ether can be prepared from synthesis gas with one step (using a bifunctional catalyst, methanol synthesis and methanol dehydration occur in one reactor) or can be synthesized by methanol dehydration. The synthesis gas may be prepared with non-petroleum energies, such as coal, biomass, natural gas, etc. If synthesizing ethanol at the same time of coproducing an amount of methanol can be achieved, methanol may not only be used as the final product, but also may be dehydrated to generate dimethyl ether. Dimethyl ether is carbonylated to generate methyl acetate, and methyl acetate is hydrogenated to generate the final product ethanol. The proportions of ethanol and methanol may be adjusted according to market demand to improve the flexibility of products and the operational motility of apparatuses, which has important realistic sense for developing new coal chemical industry. Therefore, a method for synthesizing ethanol and coproducing methanol under a co-feeding condition of synthesis gas and acetate is needed to be developed in the art.

SUMMARY OF THE INVENTION

An object of this disclosure is to provide a method for producing ethanol and coproducing methanol using synthesis gas and acetate under a co-feeding condition.

Therefore, this disclosure provides a method for producing ethanol and coproducing methanol, characterized in that the method comprises the step of passing a raw material gas containing an acetate and a synthesis gas through a reactor loaded with a catalyst to produce ethanol and coproduce methanol under the conditions of a reaction temperature of 150-350° C., a reaction pressure of 0.1-20.0 MPa, a reaction volume hourly space velocity of 100-45000 $mlg^{-1}h^{-1}$, and an acetate weight hourly space velocity of 0.01-5.0 h$^{-1}$; and the active components of the catalyst are copper and optionally zinc and/or aluminum.

In one preferred embodiment, the acetate is methyl acetate and/or ethyl acetate.

In one preferred embodiment, in the catalyst, the active component copper comprises 50.0-100.0 wt % of the total weight of the catalyst in terms of CuO; the active component zinc comprises 0-35.0 wt % of the total weight of the catalyst in terms of ZnO; and the active component aluminum comprises 0-10.0 wt % of the total weight of the catalyst in terms of Al$_2$O$_3$.

In one preferred embodiment, the catalyst further contains one or more of manganese, molybdenum, zirconium, chromium, iron, barium, magnesium, nickel, and calcium as a promoter. Preferably, the promoter comprises 0-5.0 wt % of the total weight of the catalyst in terms of the metal oxide thereof.

In one preferred embodiment, the catalyst is subjected to reduction treatment with hydrogen gas and/or a synthesis gas before use.

In one preferred embodiment, the molar ratio of synthesis gas/acetate in the raw material gas is 10-101/0.1-4, and the molar ratio of hydrogen gas/carbon monoxide in the synthesis gas is 9-100/1. Preferably, the molar ratio of synthesis gas/acetate is 21-101/2-4, and the molar ratio of hydrogen gas/carbon monoxide in the synthesis gas is 20-100/1.

In one preferred embodiment, the reaction temperature is 180-300° C., the reaction pressure is 1.0-10.0 MPa, the reaction volume hourly space velocity is 400-35000 mlg$^{-1}$h$^{-1}$, and the acetate weight hourly space velocity is 0.1-3.0 h$^{-1}$.

By using a co-feed of synthesis gas and acetate as a reaction raw material, this disclosure greatly facilitates the conversion of carbon monoxide to methanol, while an extremely high activity of acetate hydrogenation is maintained. The method of this disclosure produces ethanol while a certain amount of methanol is coproduced, and the proportions of ethanol and methanol may be adjusted, which increases the flexibility of products.

DETAILED DESCRIPTION OF THE INVENTION

In the method of this disclosure, a raw material gas containing an acetate and a synthesis gas is passed through a reactor loaded with a catalyst to produce ethanol and coproduce methanol under the conditions of a reaction temperature of 150-350° C., a reaction pressure of 0.1-20.0 MPa, a reaction volume hourly space velocity of 100-45000 mlg$^{-1}$h$^{-1}$, and an acetate weight hourly space velocity of 0.01-5.0 h$^{-1}$; and the active components of the catalyst are copper, and zinc and/or aluminum may also be contained.

Preferably, the acetate is methyl acetate and/or ethyl acetate.

Preferably, in the catalyst, the active component is copper, and the content thereof comprises 50.0-100.0 wt % of the total weight of the catalyst in terms of metal oxide; the promoter zinc comprise 0-35.0 wt % of the total weight of the catalyst in terms of metal oxide; and the promoter aluminum comprise 0-10.0 wt % of the total weight of the catalyst in terms of metal oxide.

Preferably, in the catalyst, one or a composition of several of manganese, molybdenum, zirconium, chromium, iron, barium, magnesium, nickel, and calcium may be further contained as a promoter. Preferably, it comprises 0-5.0 wt % of the total weight of the catalyst in terms of its metal oxide (for example, MnO, Cr$_2$O$_3$, Fe$_2$O$_3$, MgO, NiO, etc.).

Preferably, the catalyst is firstly subjected to reduction treatment with hydrogen gas and/or synthesis gas before reaction. It is subjected to reduction treatment for 5-60 hours with 1-100% H$_2$ or synthesis gas (H$_2$/CO=0.5-50) under a condition where the temperature is 180-350° C. and the pressure is 0.1-5.0 MPa.

Preferably, the molar ratio of synthesis gas/acetate in the raw material gas is 10-101/0.1-4, and the molar ratio of hydrogen gas/carbon monoxide in the synthesis gas is 9-100/1. Further preferable ranges are as follows: the molar ratio of synthesis gas/acetate is 21-101/2-4, and the molar ratio of hydrogen gas/carbon monoxide in the synthesis gas is 20-100/1.

The preferable reaction conditions are as follows: the reaction temperature is 180-300° C., the reaction pressure is 1.0-10.0 MPa, the reaction volume hourly space velocity is 400-35000 mlg$^{-1}$h$^{-1}$, and the acetate weight hourly space velocity is 0.1-3.0 h$^{-1}$.

The catalyst of this disclosure (also referred to as a copper-based catalyst) is preferably prepared by co-precipitation method, which comprises the following steps of:

a) adding a solution containing ions of Cu$^{2+}$ and/or optionally Zn$^{2+}$ and/or Al$^{3+}$ to a solution of a precipitating agent at 25-60° C., and stirring the resultant precipitate until it is uniform, wherein the resultant precipitate has a pH value of 7.0-10.0;

b) treating the precipitate obtained in step a) by aging for 5-60 hours, drying at 80-160° C., and calcining at 240-500° C. to obtain a calcined sample; and c) optionally placing the calcined sample obtained in step b) in a salt solution containing any one or more metals of the components of manganese, molybdenum, zirconium, chromium, iron, barium, magnesium, nickel, and calcium and impregnating for one or more times, drying at 80-160° C. after the completion of impregnation, and calcining at 240-500° C. to obtain the copper-based catalyst.

This disclosure mainly has the advantage that a catalyst for preparing ethanol and coproducing methanol with a co-feed of synthesis gas and acetate is prepared by using inexpensive raw materials and utilizing a simple co-precipitation method, and this process facilitates the conversion of carbon monoxide to methanol, while an extremely high activity of acetate hydrogenation is maintained. The proportions of ethanol and methanol may be adjusted by changing reaction conditions, and a new reaction process is developed, which increases the flexibility of products.

This present disclosure will be described in detail below by Examples, but this disclosure is not limited to these Examples.

Example 1: Preparation of Catalysts

1) Preparation of 100% CuO Catalyst 121 g of Cu(NO$_3$)$_2$.3H$_2$O was dissolved in 2000 ml of deionized water, and 68.0 g of concentrated aqueous ammonia (25-28%) was diluted with 1500 ml of deionized water. The aqueous ammonia solution was vigorously stirred at room temperature, and this aqueous metal nitrate solution was slowly added to the aqueous ammonia solution in about 60 min. The pH value of the precipitate was adjusted to 10.0 using the aqueous ammonia solution, stirring was continued for 200 min, and then aging was performed for 36h. The precipitate was washed to neutral with deionized water and was separated by centrifugation. The resultant precipitate was dried in an oven at 120° C. for 24h, the sample was placed in a muffle furnace after drying and was warmed up to 400° C. at a temperature increase rate of 1° C./min, calcination was performed for 5h to obtain a calcined sample. This catalyst was denoted by CAT1.

2) Preparation of 85% CuO/10% ZnO/5% $Al_2O_3$ catalyst 102.85 g of $Cu(NO_3)_2 \cdot 3H_2O$, 12.00 g of $Zn(NO_3)_2 \cdot 6H_2O$, and 14.71 g of $Al(NO_3)_3 \cdot 9H_2O$ were dissolved in 2000 ml of deionized water, 72.52 g of concentrated aqueous ammonia (25-28%) was diluted with 1500 ml of deionized water. The aqueous ammonia solution was vigorously stirred at room temperature, and the mixed aqueous metal nitrate solutions were slowly added to the aqueous ammonia solution in about 60 min. The pH value of the precipitate was adjusted to 10.0 using the aqueous ammonia solution, stirring was continued for 200 min, and then aging was performed for 36h. The precipitate was washed to neutral with deionized water and was separated by centrifugation. The resultant precipitate was dried in an oven at 120° C. for 24h, the sample was placed in a muffle furnace after drying and was warmed up to 400° C. at a temperature increase rate of 1° C./min, calcination of sample was performed for 5h to obtain a calcined sample. This catalyst was denoted by CAT3.

3) Preparation of 75% CuO/13% ZnO/5% $Al_2O_3$/1% MnO/1% NiO Catalyst 96.80 g of $Cu(NO_3)_2 \cdot 3H_2O$, 15.60 g of $Zn(NO_3)_2 \cdot 6H_2O$, and 14.71 g of $Al(NO_3)_3 \cdot 9H_2O$ were dissolved in 2000 ml of deionized water, 72.62 g of concentrated aqueous ammonia (25-28%) was diluted with 1500 ml of deionized water. The aqueous ammonia solution was vigorously stirred at room temperature, and the mixed aqueous metal nitrate solutions were slowly added to the aqueous ammonia solution in about 60 min. The pH value of the precipitate was adjusted to 10.0 using the aqueous ammonia solution, stirring was continued for 200 min, and then aging was performed for 36h. The precipitate was washed to neutral with deionized water and was separated by centrifugation. The resultant precipitate was dried in an oven at 120° C. for 24h, the sample was placed in a muffle furnace after drying and was warmed up to 400° C. at a temperature increase rate of 1° C./min, calcination of sample was performed for 5h to obtain a calcined sample. 1.41 g of $Mn(NO_3)_2 \cdot 4H_2O$ and 1.36 g of $Ni(NO_3)_2 \cdot 4H_2O$ were further dissolved in 50 ml of deionized water, and the aqueous solutions of manganese and nickel were loaded on the calcined sample using an impregnation method, and the excessive solvent was evaporated off at 80° C. Drying was performed in an oven at 120° C. for 24h, the sample was placed in a muffle furnace after drying and was warmed up to 400° C. at a temperature increase rate of 1° C./min, calcination of sample was performed for 3h to obtain a catalyst sample. This catalyst was denoted by CAT4.

The preparation of the other catalysts CAT2 and CAT5-10 are similar to those of CAT3 and CAT4. The relationship between specific preparation conditions and the numbers of catalysts can be seen in Table 1. Compositions of catalysts measured by XRF (X-ray fluorescence spectrometry, PANalytical Corporation, Netherlands) can be seen in Table 2.

TABLE 1

Preparation of catalysts

| Catalyst No. | Name and mass of raw materials (g) | | | | | |
|---|---|---|---|---|---|---|
| | $Cu(NO_3)_2 \cdot 3H_2O$ | $Zn(NO_3)_2 \cdot 6H_2O$ | $Al(NO_3)_3 \cdot 9H_2O$ | $Mn(NO_3)_2 \cdot 4H_2O$ | $Ni(NO_3)_2 \cdot 4H_2O$ | $Cr(NO_3)_3 \cdot 9H_2O$ |
| CAT1 | 121.00 | — | — | — | — | — |
| CAT2 | 108.90 | 12.00 | — | — | — | — |
| CAT3 | 102.85 | 12.00 | 14.71 | — | — | — |
| CAT4 | 96.80 | 15.60 | 14.71 | 1.41 | 1.36 | — |
| CAT5 | 90.75 | 18.00 | 20.59 | — | — | 9.41 |
| CAT6 | 90.75 | 18.00 | 20.59 | — | — | — |
| CAT7 | 84.70 | 24.00 | 23.53 | — | — | — |
| CAT8 | 84.70 | 24.00 | 20.59 | 1.41 | — | — |
| CAT9 | 72.60 | 30.00 | 29.41 | — | 2.72 | 9.41 |
| CAT10 | 60.50 | 42.00 | 29.41 | — | — | — |

| Catalyst No. | Name and mass of raw materials (g) | | | | | | Aqueous ammonia (25-28%) |
|---|---|---|---|---|---|---|---|
| | $Fe(NO_3)_3 \cdot 9H_2O$ | $(NH_4)_2MoO_4$ | $Mg(NO_3)_2 \cdot 6H_2O$ | $Ca(NO_3)_2$ | $Zr(NO_3)_4 \cdot 5H_2O$ | $Ba(NO_3)_2$ | |
| CAT1 | — | — | — | — | — | — | 68.00 |
| CAT2 | — | — | — | — | — | — | 67.92 |
| CAT3 | — | — | — | — | — | — | 72.52 |
| CAT4 | — | — | — | — | — | — | 72.62 |
| CAT5 | 2.02 | — | — | — | — | — | 78.09 |
| CAT6 | — | 0.57 | 5.12 | — | — | — | 75.55 |
| CAT7 | — | — | — | 1.69 | 1.40 | — | 75.69 |
| CAT8 | 2.02 | — | — | — | — | 0.68 | 73.60 |
| CAT9 | — | 0.57 | — | — | — | — | 80.40 |
| CAT10 | — | — | 2.56 | 1.69 | 2.80 | 0.68 | 77.97 |

TABLE 2

Compositions of catalysts measured by XRF

| Catalyst No. | Composition of catalyst (%) | | | | | | | | | | | |
|---|---|---|---|---|---|---|---|---|---|---|---|---|
| | CuO | ZnO | $Al_2O_3$ | MnO | NiO | $Cr_2O_3$ | $Fe_2O_3$ | $MoO_3$ | MgO | CaO | $ZrO_2$ | BaO |
| CAT1 | 100 | — | — | — | — | — | — | — | — | — | — | — |
| CAT2 | 90.4 | 9.6 | — | — | — | — | — | — | — | — | — | — |
| CAT3 | 84.7 | 10.4 | 4.9 | — | — | — | — | — | — | — | — | — |
| CAT4 | 80.2 | 12.9 | 5.2 | 0.9 | 0.8 | — | — | — | — | — | — | — |
| CAT5 | 75.3 | 14.8 | 7.1 | — | — | 1.7 | 1.1 | — | — | — | — | — |
| CAT6 | 75.1 | 15.2 | 6.8 | — | — | — | — | 1.1 | 1.8 | — | — | — |
| CAT7 | 70.0 | 19.6 | 8.2 | — | — | — | — | — | — | 1.2 | 1.0 | — |
| CAT8 | 69.5 | 20.3 | 7.0 | 0.9 | — | — | 1.2 | — | — | — | — | 1.1 |
| CAT9 | 60.2 | 25.1 | 9.6 | — | 2.1 | 1.9 | — | 1.1 | — | — | — | — |
| CAT10 | 50.3 | 34.7 | 10.1 | — | — | — | — | — | 0.9 | 1.1 | 2.1 | 0.8 |

Example 2: Evaluation of Catalysts

The reaction volume hourly space velocity in this disclosure was defined by the volumetric flow rate of the reaction raw materials (under a standard condition) passed into a reaction system per hour being divided by the mass of a catalyst. It was represented by GHSV with a unit of $mlg^{-1} h^{-1}$.

10 g of the above catalyst, which was screened to 20-40 mesh, was filled into a thermostatic zone of a fixed bed reactor. Before reaction, the catalyst was subjected to online reduction, wherein the reduction temperature is 260° C., the pressure is 0.1 MPa, the reducing gas is 5% $H_2$+95% $N_2$, and the reduction time is 24h. After reduction, temperature was reduced to 230° C., and $H_2$ remaining in pipelines and the reactor was purged with $N_2$. The gas was then changed to synthesis gas with a certain composition and pressure, and a mass flowmeter was adjusted to a designated flow rate (standard condition). A high-pressure acetate feed pump was set to a designated flow rate, and the reaction begun after the temperature and the pressure were stable. The product was subjected to online analysis, and was sampled once per hour. Pipelines and back pressure valve were all heated to maintain temperature from an outlet of the reactor to an inlet of a ten-way valve of a gas chromatograph.

Analytical Method of Products
Chromatograph: Agilent 7890A
FID chromatographic column: HP-PLOT-Q 19091P-Q04, 30 m×0.32 mm (inner diameter), a film thickness of 20 μm
Carrier gas: helium gas, 2 ml/min
Column temperature: 50° C.–240° C., 10° C./min
240° C., which is maintained for 15 min
Feed port: split (50:1); temperature: 250° C.
Detector: FID; temperature: 300° C.
TCD chromatographic column: carbon molecular sieve column, TDX-01 2 m×2 mm (inner diameter)
Carrier gas: helium gas, 35 ml/min
Column temperature: 50° C.–240° C., 10° C./min
240° C., which is maintained for 15 min
Feed port: septum purge at the feed port; temperature: 250° C.
Detector: TCD; temperature: 300° C.
1) The activities of catalysts with different compositions under a co-feeding condition of synthesis gas (the volumetric composition was 80% $H_2$/4% CO and other gases) and methyl acetate (MAc) can be seen in Table 3.

Reaction Conditions were as follows: the reaction temperature was 240° C., the reaction pressure was 4.5 MPa, the molar composition of the raw material gas was $H_2$/CO/MAc=20/1/4 (80% $H_2$/4% CO/16% MAc), the total gas hourly space velocity (GHSV)=5676 $mlg^{-1}h^{-1}$, and methyl acetate weight hourly space velocity ($WHSV_{MAc}$)=3.0$h^{-1}$.

TABLE 3

Performances of reactions for preparing ethanol and coproducing methanol by co-feeding synthesis gas and methyl acetate on different catalysts

| | Hydrogenation reaction of methyl acetate | | | |
|---|---|---|---|---|
| Catalyst No. | Conversion rate of methyl acetate (carbon mol %) | Selectivity of ethanol (mol %) | Selectivity of methanol[a] (mol %) | Conversion rate of CO[b] (mol %) |
| CAT1 | 80.4 | 45.4 | 50.5 | 51.3 |
| CAT2 | 85.7 | 45.8 | 50.6 | 53.8 |
| CAT3 | 86.5 | 46.7 | 50.1 | 56.9 |
| CAT4 | 88.6. | 46.6 | 49.9 | 57.3 |
| CAT5 | 88.2 | 46.6 | 50.4 | 55.8 |
| CAT6 | 87.9 | 46.2 | 50.5 | 56.1 |
| CAT7 | 84.2 | 46.8 | 49.7 | 55.2 |
| CAT8 | 85.1 | 46.6 | 50.5 | 54.7 |

TABLE 3-continued

Performances of reactions for preparing ethanol and coproducing methanol by co-feeding synthesis gas and methyl acetate on different catalysts

| | Hydrogenation reaction of methyl acetate | | | |
|---|---|---|---|---|
| Catalyst No. | Conversion rate of methyl acetate (carbon mol %) | Selectivity of ethanol (mol %) | Selectivity of methanol[a] (mol %) | Conversion rate of CO[b] (mol %) |
| CAT9 | 81.5 | 46.2 | 49.6 | 52.4 |
| CAT10 | 80.6 | 45.9 | 50.2 | 50.7 |

[a] $\text{Selectivity of methanol} = \dfrac{\text{molar percentage content of methanol}}{\sum \text{molar percentage content of each product of methyl acetate hydrogenation}} \times 100\%$ (notes: this selectivity excluded the methanol generated by CO hydrogenation).

[b] In CO hydrogenation reaction, the selectivity of methanol was 100% and no byproduct was generated.

2) The performances of catalyst CAT5 at different temperatures in co-feeding synthesis gas (the volumetric composition was 98.9% $H_2$/0.99% CO and other gases) and methyl acetate (MAc) can be seen in Table 4.

Reaction Conditions were as follows: the reaction pressure was 5.5 MPa, the molar composition of the raw material gas was $H_2$/CO/MAc=1000/10/1 (98.9% $H_2$/0.99% CO/0.11% MAc), the total gas hourly space velocity (GHSV)=35000 ml$g^{-1}h^{-1}$, and methyl acetate weight hourly space velocity (WHSV$_{MAc}$)=0.127$h^{-1}$.

TABLE 4

Effects of reaction temperature on the performances for preparing ethanol and coproducing methanol by co-feeding synthesis gas and methyl acetate using CAT5 catalyst

| | Hydrogenation reaction of methyl acetate | | | |
|---|---|---|---|---|
| Reaction temperature °C. | Conversion rate of methyl acetate (C mol %) | Selectivity of ethanol (mol %) | Selectivity of methanol[a] (mol %) | Conversion rate of CO[b] (mol %) |
| 180 | 68.1 | 39.7 | 53.2 | 45.3 |
| 200 | 77.4 | 41.0 | 51.8 | 51.2 |
| 220 | 88.3 | 43.3 | 50.1 | 55.8 |
| 230 | 94.5 | 43.9 | 49.9 | 59.7 |
| 240 | 96.2 | 45.2 | 50.3 | 63.3 |
| 250 | 97.3 | 46.7 | 49.3 | 66.6 |
| 270 | 98.1 | 48.5 | 48.8 | 71.2 |
| 290 | 98.8 | 49.3 | 48.4 | 74.5 |
| 300 | 99.4 | 49.8 | 47.8 | 76.4 |

[a] $\text{Selectivity of methanol} = \dfrac{\text{molar percentage content of methanol}}{\sum \text{molar percentage content of each product of methyl acetate hydrogenation}} \times 100\%$ (notes: this selectivity excluded the methanol generated by CO hydrogenation).

[b] In CO hydrogenation reaction, the selectivity of methanol was 100% and no byproduct was generated.

3) The performances of catalyst CAT3 at different pressures in co-feeding synthesis gas (the volumetric composition was 95.2% $H_2$/1.4% CO and other gases) and methyl acetate can be seen in Table 5.

Reaction Conditions were as follows: the reaction temperature was 250° C., the molar composition of the raw material gas was $H_2$/CO/MAc=70/1/2.5 (95.2% $H_2$/1.4% CO/3.4% MAc), the total gas hourly space velocity (GHSV)=19587 ml$g^{-1}h^{-1}$, and methyl acetate weight hourly space velocity (WHSV$_{MAc}$)=2.2$h^{-1}$.

TABLE 5

Effects of reaction pressure on performances for preparing ethanol and coproducing methanol by co-feeding synthesis gas and methyl acetate using catalyst CAT3

| | Hydrogenation reaction of methyl acetate | | | |
|---|---|---|---|---|
| Reaction pressure (MPa) | Conversion rate of methyl acetate (C mol %) | Selectivity of ethanol (mol %) | Selectivity of methanol[a] (mol %) | Conversion rate of CO[b] (mol %) |
| 1.0 | 88.5 | 42.8 | 51.0 | 53.6 |
| 3.0 | 91.3 | 44.3 | 50.7 | 54.8 |
| 5.0 | 93.7 | 46.6 | 49.7 | 57.3 |
| 7.0 | 96.9 | 47.1 | 48.5 | 60.9 |
| 9.0 | 97.7 | 46.8 | 49.2 | 64.7 |
| 10.0 | 97.6 | 47.3 | 47.5 | 66.5 |

[a] Selectivity of methanol = $\dfrac{\text{molar percentage content of methanol}}{\sum \text{molar percentage content of each product of methyl acetate hydrogenation}} \times 100\%$ (notes: this selectivity excluded the methanol generated by CO hydrogenation).
[b] In CO hydrogenation reaction, the selectivity of methanol was 100% and no byproduct was generated.

4) Performances of different catalysts under different reaction conditions in co-feeding synthesis gas and ethyl acetate can be seen in Table 6.

TABLE 6

Performances for preparing ethanol and coproducing methanol by co-feeding synthesis gas and ethyl acetate using different catalysts under different reaction conditions

| | Reaction conditions | | | | | Hydrogenation reaction of ethyl acetate | | |
|---|---|---|---|---|---|---|---|---|
| Catalyst No. | Temperature (° C.) | Pressure (MPa) | Space velocity (mlg$^{-1}$h$^{-1}$) | H2/CO/EAc (mol) | EAc weight hourly space velocity (h$^{-1}$) | Conversion rate of ethyl acetate (carbon mol %) | Selectivity of ethanol[a] (mol %) | Conversion rate of CO[b] (mol %) |
| CAT2 | 230 | 3.0 | 20364 | 30/1/1 | 2.5 | 83.6 | 98.7 | 54.2 |
| CAT3 | 250 | 4.5 | 15135 | 35/1/1.5 | 2.0 | 90.6 | 98.4 | 62.8 |
| CAT4 | 220 | 5.0 | 400 | 9/1/2.5 | 0.26 | 77.3 | 97.2 | 45.1 |
| CAT5 | 210 | 4.0 | 11261 | 60/1/1 | 0.6 | 82.7 | 98.5 | 40.8 |
| CAT7 | 240 | 6.0 | 1663 | 160/2/3 | 0.1 | 85.1 | 97.3 | 58.7 |
| CAT9 | 270 | 7.0 | 8655 | 80/1/4 | 1.6 | 94.2 | 98.9 | 65.9 |

[a] Selectivity of methanol = $\dfrac{\text{molar percentage content of methanol}}{\sum \text{molar percentage content of each product of methyl acetate hydrogenation}} \times 100\%$ (notes: this selectivity excluded the methanol generated by CO hydrogenation).
[b] In CO hydrogenation reaction, the selectivity of methanol was 100% and no byproduct was generated.

The following conclusions can be obtained according to above Examples and data:

When a certain amount of co-feed of synthesis gas and acetate is used as a reaction raw material, it is possible to effectively synthesize ethanol and coproduce a small amount of methanol in a reactor on a specific catalyst; the coproduced methanol may be either used as a product alone or dehydrated to produce dimethyl ether, and methyl acetate, carbonylated product of dimethyl ether, is hydrogenated to produce ethanol; and the proportions of ethanol and methanol may be adjusted by changing the feed ratio of carbon monoxide, hydrogen gas in the synthesis gas, and acetate so as to improve the operational flexibility of apparatuses and the market adaptability.

This disclosure has the advantage that it is possible to effectively synthesize ethanol and coproduce methanol in a reactor on an inexpensive and easily available catalyst by using an amount of a co-feed of synthesis gas and acetate as a raw material under proper reaction conditions. Compared to the conventional methanol synthesis, this disclosure facilitates the reaction for converting carbon monoxide to methanol, while a high-efficiency reactivity of acetate hydrogenation is maintained. This disclosure provides a new scheme to the development of the coal chemical industry.

It is to be indicated that, with respect to the person skilled in the art, various modifications may be made to these Examples without departing from the technical principle of this disclosure. These modifications should also be considered to be within the scope, which should be protected by this disclosure.

What is claimed is:

1. A method for producing ethanol and coproducing methanol, comprising passing a raw material gas containing an acetate and a synthesis gas through a reactor loaded with a catalyst to produce ethanol and coproduce methanol under conditions of a reaction temperature of 150-350° C., a reaction pressure of 0.1-20.0 MPa, a reaction volume space velocity of 100-45000 mlg$^{-1}$h$^{-1}$, and an acetate weight hourly space velocity of 0.01-5.0 h$^{-1}$; and the catalyst comprises, based on weight, about 80%-85% CuO, about 10%-15% ZnO, and about 5%-10% $Al_2O_3$.

2. The method according to claim 1, wherein the acetate is methyl acetate and/or ethyl acetate.

3. The method according to claim 1, wherein the catalyst further contains one or more of manganese, molybdenum, zirconium, chromium, iron, barium, magnesium, nickel, and calcium as a promoter.

4. The method according to claim 3, wherein the catalyst comprises no more than 5% metal oxide of the promoter.

5. The method according to claim 1, wherein the catalyst is subjected to reduction treatment with hydrogen gas and/or a synthesis gas before use.

6. The method according to claim 1, wherein the molar ratio of synthesis gas/acetate in the raw material gas is 10-101/0.1-4, and the molar ratio of hydrogen gas/carbon monoxide in the synthesis gas is 9-100/1.

7. The method according to claim 1, wherein the molar ratio of synthesis gas/acetate in the raw material gas is 21-101/2-4, and the molar ratio of hydrogen gas/carbon monoxide in the synthesis gas is 20-100/1.

8. The method according to claim 1, wherein the reaction temperature is 180-300° C., the reaction pressure is 1.0-10.0 MPa, the reaction volume hourly space velocity is 400-35000 $mlg^{-1}h^{-1}$, and the acetate weight hourly space velocity is 0.1-3.0 $h^{-1}$.

\* \* \* \* \*